US006984410B2

(12) United States Patent
Vogt et al.

(10) Patent No.: US 6,984,410 B2
(45) Date of Patent: Jan. 10, 2006

(54) PROCESS FOR ANTIBIOTIC COATING OF ELEMENTS WITH INTERCONNECTING MICROCAVITIES, ELEMENTS THUS COATED AS WELL AS THEIR USAGE

(75) Inventors: Sebastian Vogt, Jena (DE); Matthias Schnabelrauch, Jena (DE); Klaus-Dieter Kühn, Marburg (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 69 days.

(21) Appl. No.: 10/217,788

(22) Filed: Aug. 13, 2002

(65) Prior Publication Data
US 2003/0096097 A1 May 22, 2003

(30) Foreign Application Priority Data
Aug. 31, 2001 (DE) .................... 101 42 465
Feb. 1, 2002 (DE) .................... 102 04 307

(51) Int. Cl.
*B05D 3/00* (2006.01)
(52) U.S. Cl. .................. 427/2.1; 427/2.24; 427/421; 427/430.1; 427/435
(58) Field of Classification Search ................. 427/2.1, 427/2.24, 2.25, 2.26, 2.28, 2.29, 2.3, 2.31, 427/421, 430.1, 435
See application file for complete search history.

(56) References Cited

U.S. PATENT DOCUMENTS

| 4,322,398 A | 3/1982 | Reiner et al. ............... 424/19 |
| 4,617,293 A | 10/1986 | Wahlig et al. ............... 514/41 |
| 5,607,685 A | 3/1997 | Cimbollek et al. .......... 424/422 |
| 5,679,646 A | 10/1997 | Cimbollek et al. ........... 514/43 |
| 5,902,283 A * | 5/1999 | Darouiche et al. .......... 604/265 |
| 2002/0183265 A1 | 12/2002 | Vogt et al. .................... 514/29 |

FOREIGN PATENT DOCUMENTS

| DE | 44 04 018 A1 | 8/1995 |
| DE | 101 14 245 A1 | 10/2002 |
| EP | 0 087 662 | 9/1983 |
| GB | 1 400 464 | 7/1975 |
| GB | 1 478 240 | 6/1977 |
| WO | 97 38698 | 10/1997 |

OTHER PUBLICATIONS

Hackh's Chemical Dictionary, 4th edition, p. 537, 1969.*
Abstract of EP 0087662 from EPO website database.

* cited by examiner

Primary Examiner—Bret Chen
(74) Attorney, Agent, or Firm—Norris McLaughlin & Marcue PA

(57) ABSTRACT

The invention concerns the manufacture of an antibiotic coating of elements with interconnecting microcavities, elements thus coated as well as their use. In a preferred embodiment, a homogenous solution of a gentamicin derivative in a solvent is introduced into the microcavities of non-metallic elements with interconnecting microcavities through dipping, spraying and dripping, and following evaporation or vaporization of the solvent, a layer of the gentamicin derivative is formed on the surface of the microcavities.

14 Claims, No Drawings

PROCESS FOR ANTIBIOTIC COATING OF ELEMENTS WITH INTERCONNECTING MICROCAVITIES, ELEMENTS THUS COATED AS WELL AS THEIR USAGE

The present invention concerns a process for antibiotic coating of elements with interconnecting microcavities, substances so coated as well as their usage.

These antibiotic provided substances with interconnecting microcavities should find use as implants in human and veterinary medicine for the treatment of bone defects and, if need be, for the treatment of soft tissue damage. Here a continuous antibiotic release from antibiotic coating situated on the internal surface of the interconnecting microcavities over a time period of several days is sought so that a microbial infection in the region of the bone defect and/or soft part defect to be treated can be effectively prevented or combated.

Bone defects occur relatively frequently in human and veterinary medicine and are in particular caused by bone fistulae, comminuted fractures and tumors. In case of open comminuted fractures and, frequently, additional infections of the bone tissue are observed. The treatment of bone defects can take place by replenishment with suitable implants. In recent years, porous implants, which have an osteo-conductive action on account of their chemical composition and their porosity, have especially been found to be of interest and favor for growing of the surrounding bone tissue. The treatment of bone defects is always problematic when in addition microbial infections of the bone tissue are present. Infections of the bone tissue can be combated by systemic or local applications of suitable antibiotics. The systemic use of antibiotics is problematic owing to the occasionally not inconsiderable toxicity of the antibiotics. The local application directly in or on the infected tissue, in contrast, offers the advantage that high local antibiotic concentrations can be achieved while avoiding harmful antibiotic concentrations in the rest of the body. Through these high local antibiotic concentrations at the site of the bacterial infection, an almost complete killing off of the microorganisms is possible, so that the bacterial infections are treated very effectively. It is especially advantageous if an effective antibiotic concentration is maintained at the site of the bacterial infection over a period of several days to weeks so that the antibiotic can penetrate into the infected tissue as deeply as possible, and in this way, hardly accessible germs are also eliminated. Soft tissue damage with bacterial infections can likewise frequently be found in human and veterinary medicine. Local antibiotic treatment for treatment of these infections is therefore also of interest.

Previously, lightly water-soluble salts of aminoglycoside antibiotics found relatively little notice in the manufacture of depot preparations and antibiotically active implants. A series of lightly soluble salts is known. Thus, with gentamicin, the preparation of lightly soluble salts based on higher fatty acids and aryl alkyl carboxylic acids was publicized. (G. M. Luedemann, M. J. Weinstein: Gentamicin and method of production. Jul. 16, 1962, U.S. Pat. No. 3,091, 572). Example of this are gentamicin salts of lauric acid, stearic acid, palmitic acid, oleic acid, phenyl butyric acid, and naphthalene-1-carboxylic acid. The synthesis of dodecyl sulfate of gentamicin in diluted or diluted-methanol solution has been described by Jurado Soler et al. (A. Jurado Soler, J. A. Ortiz Hernandez, C. Ciuro Bertran: New Gentamicin Derivatives; Method of Manufacture of the Same and Antibiotically Active Composition Containing Them. Sep. 30, 1974, DE 24 46 640). These salts, nonetheless, prove in many ways to be disadvantageous because they represent waxy, hydrophobic substances which prevent a galenic use. Jurado Soler et al. found that gentamicin pentakis dodecyl sulfate is soluble in solvents such as methanol, ethanol and dimethyl sulfoxide. They used gentamicin pentakis dodecyl sulfate for producing injection preparations, salves and creams. Further possible uses of gentamicin pentakis dodecyl sulfate were not considered. Fatty acid salts and aliphatic sulfates of gentamicin and etamycin were synthesized from the free base or from their salts in water at 50 to 80° C. (H. Voege, P. Stadler, H. J. Zeiler, S. Samaan, K. G. Metzger: Barely Soluble Salts of Aminoglycosides as Well as Formulations Containing These With Delayed Active Ingredient Release, Dec. 28, 1982, DE 32 48 328). These antibiotic fatty acid salts should be suitable as injection substances. Barely soluble aminoglycoside flavonoid phosphates (H. Wahlig, E. Dingeldein, R. Kirchlechner, D. Orth, W. Rogalski: Flavonoid phosphate salts of aminoglycoside antibiotics. Oct. 13, 1986, U.S. Pat. No. 4,617,293) represent a more recent development. Salts of the phosphoric acid monoester of derivatives of hydroxy flavanes, hydroxy flavenes, hydroxy flavones and hydroxy flavylium are described. Derivatives of flavanones and flavones are especially preferred in this connection. These barely soluble salts are supposed to find use as depot preparations. Thus, for example, these salts are introduced into collagen fleece (H. Wahlig, E. Dingeldein, D. Braun: Medicinally useful, fleece made of collagen resorbable in the body. Sep. 22, 1981, U.S. Pat. No. 4,291,013).

The creation of simple antibiotic(s) deposits in the pore systems of porous elements by steeping porous elements with diluted antibiotics solutions is a general state of knowledge (R. Reiner, W. Kiβing, H. Dörnig, K. Köster, H. Heide: Implantable Pharmaceutical Deposit. Feb. 20, 1978, DE 2807132). Here a retarded active ingredient release of the easily water soluble antibiotics can be attained by adsorption and/or diffusion processes, which depends upon the material used, the pore volume and porosity. In addition, it is also possible to dissolve lightly water soluble antibiotics salts in suitable organic solvents and to steep the molded elements with these solutions. In this way, active ingredient deposits arise in the molded substances which manifest a retarded active ingredient release. An example of this is the method described by Cimbollek and Nies on the solution of a lightly water-soluble gentamicin salt and its use for coating (M. Cimbollek, B. Nies: Solvent For Lightly Soluble Gentamicin Salt. May 4, 1994, U.S. Pat. No. 5,679,646). This gentamicin salt was synthesized on the basis of 3-p-methoxy benzylidene-6-hydroxy-4'-methoxy flavanone-6-phosphate. A very interesting process is described by Kurtz where lightly water soluble antibiotics salts which are built up of gentamicin or polymycin and penicillin or cephalosporin are dissolved in an organic solvent, and substrates not specified in greater detail are steeped with these solutions (L. D. Kurtz: Water-insoluble biocidal antibiotics salts. Nov. 13, 1973, DE 23 01 633). The penicillin or cephalosporin radicals form the anionic components of the salts and the aminoglycoside radicals the cationic components.

In summary, it can be stated that up until now, no methods were known with which antibiotic components could applied on the surface of interconnecting microcavities which consist of lightly water-soluble gentamicin salts which contain an anionic radical from the alkyl sulfates and/or alkyl sulfonates group. The layer-forming properties of lightly water-soluble antibiotics salts on the basis of organic sulfates and sulfonates has found no notice until now.

Underlying the present invention is the objective of developing improved elements with antibiotic coating as well as a simple, cost efficient manufacturing process for antibiotic coating of elements with interconnecting microcavities. These antibiotically outfitted substances with interconnecting microcavities should find use as implants for the treatment of bone and soft tissue damage in human and veterinary medicine. With this method, while dispensing with polymer binding agents, antibiotic coatings should be created simply so that they will make possible an antibiotics release over a period of several days. The antibiotic coating should adhere well to the inner surface of bodies with interconnecting microcavities, and may not occlude the interconnecting microcavities.

The objective is accomplished by the characteristics of the invention described herein. Advantageous configurations are indicated herein as well.

Underlying the invention is the surprising finding that antibiotic coatings with retarding active ingredient release in the microcavities of elements with interconnecting microcavities are especially formed by introducing into the microcavities a solution of gentamicin pentakis dodecyl sulfate or gentamicin pentakis dodecyl sulfonate in a suitable organic solvent (for example, from the alcohols group) by suitable measures such as steeping, spraying or dripping, and by a layer of gentamicin pentakis dodecyl sulfate or gentamicin pentakis dodecyl sulfonate remaining behind on the surface of the microcavities after removing the organic solvent (such as by evaporation or vaporization). The microcavities can be constructed as pores.

The substances can be of organic or inorganic nature or also be composites of inorganic and organic material. They are, for example, made of collagen, gelatin, polyesters, titanium, titanium alloys, high-grade steel, calcium carbonate, calcium sulfate, tri-calcium phosphate or hydroxyl apatite. By metallic elements with interconnecting microcavities are in particular understood such that have microcavities on their surface which are connected with one another. Metallic elements the surface of which is so roughed by sand blasting that they have open cavities connected with one another are also considered metallic elements with interconnecting microcavities. It is evident that the solutions used are as homogenous as possible. Above all, it is understood that lower alcohols as well as N,N-dimethyl formamide (DMF) or dimethyl sulfoxide (DMSO) are suitable as solvents. Methanol or ethanol are preferred solvents.

Gentamicin pentakis dodecyl sulfate, gentamicin tetrakis dodecyl sulfate, gentamicin tetrakis dodecyl sulfonate and also gentamicin pentakis dodecyl sulfonate are non-crystalline, waxy substances which manifest a certain course in connection with the evaporation or vaporization of the organic solvent, and thereby are deposited as a layer on surfaces. Surprisingly, they adhere well to glass, ceramic or plastic surfaces.

Surprisingly, clindamycin dodecyl sulfate, clindamycin dodecyl sulfonate, lincosamine dodecyl sulfate, lincosamine dodecyl sulfonate can be dissolved in methanol, ethanol, dimethyl sulfoxide and N,N-dimethyl formamide. These substances can thus be added to gentamicin solutions without any problems. Adding tetracycline dodecyl sulfate or tetracycline dodecyl sulfonate to the solutions is also possible. One can also use the dodecyl sulfates or the dodecyl sulfonates of chlortetracycline, oxytetracycline, demethyl chlortetracycline, methacycline, doxycycline, rolitetracycline and monocycline instead of tetracycline dodecyl sulfate. Ciprofloxacin dodecyl benzyl sulfonate can also be added. Correspondingly, coatings containing the gentamicin components and at least one of the mentioned additional antibiotics components rise to the surfaces of the microcavities. The manufacture of antibiotic coatings only with the dodecyl sulfates, dodecyl sulfonates and dodecyl benzyl sulfonates of the antibiotics enumerated without a gentamicin-containing antibiotic component is also within the context of this invention.

Surprisingly, other antibiotics can be mechanically fixed in place in layers of gentamicin pentakis dodecyl sulfate or gentamicin tetrakis dodecyl sulfate and gentamicin pentakis dodecyl sulfonate or gentamicin tetrakis dodecyl sulfonate by inclusion or overlaying. Therefore, it is possible for first a diluted solution which contains at least one slightly water-soluble antibiotic component from the aminoglycoside antibiotics, tetracycline antibiotics, lincosamide antibiotics and the 4-quinolone antibiotics group, and subsequently after evaporation and/or vaporization of the water, for a solution which consists of gentamicin pentakis dodecyl sulfate and/or gentamicin tetrakis dodecyl sulfate and/or gentamicin pentakis dodecyl sulfonate and/or gentamicin tetrakis dodecyl sulfonate and the solvent methanol or ethanol or dimethyl sulfoxide or N,N-dimethyl formamide to be introduced by dipping or spraying or dripping. In the end, the result is a double layer. With use in implants, the second antibiotic is first released when the gentamicin layer is at least partially dissolved. In this structural form of the invention, gentamicin sulfate, clindamycin hydrochloride, clindamycin dihydrogen phosphate, lincosamine hydrochloride, kanamycin sulfate, amikacin sulfate, tobramycin sulfate, tetracycline hydrochloride, chlortetracycline hydrochloride, oxytetracycline hydrochloride, demethyl chlortetracycline hydrochloride, methacycline hydrochloride, doxycycline hydrochloride, rolitetracycline hydrochloride, minocycline hydrochloride and/or ciprofloxacin hydrochloride and/or moxifloxacin hydrochloride are preferably used as slightly water-soluble antibiotic components.

The invention also concerns a process for the antibiotic coating of substances with interconnecting microcavities in which a solution containing one or more substances from the ciprofloxacin dodecyl benzyl sulfonate and/or moxifloxacin dodecyl sulfate and/or moxifloxacin dodecyl benzyl sulfonate and/or moxifloxacin dodecyl sulfonate and/or the dodecyl sulfates group and/or dodecyl sulfonates of clindamycin, tetracycline, lincosamine, chlortetracycline, oxytetracycline, demethyl chlortetracycline, methacycline, doxycycline, rolitetracycline and minocycline is introduced into the microcavities, and following evaporation or vaporization of the solvent, a layer of these substances arises on the surface of the microcavities.

Furthermore, it is in accordance with this invention that preferably fleece, felt fabric, hosiery and knit fabrics from polyester, collagen and gelatin are coated.

The respective dodecyl sulfate or sulfonate is preferably used in a concentration from 0.1 to 20.0 percent by mass in relation to the solvent.

It is also in accordance with the invention that preferably porous molded substances of polyesters, calcium carbonate, calcium sulfate, tricalcium phosphate, hydroxyl apatite and resorbable glass are preferably coated.

It is within the meaning of the invention that the antibiotically coated substances with interconnecting microcavities are used as implants.

The following examples explain the invention without restricting it.

EXAMPLES

The invention should be explained by Examples 1 and 2 below.

Square, resorbable phosphate glasses with dimensions of 20×20×10 mm are used for Examples 1 and 2 as elements with interconnecting microcavities. They had an overall porosity of 65 percent by volume.

Preparation of Examples 1 and 2

Gentamicin pentakis dodecyl sulfate was used for the examples, the manufacture of which took place in accordance with the method of Jurado Soler et al. (A. Jurado Soler, J. A. Ortiz Hernandez, C. Ciuro Bertran: New Gentamicin Derivatives: Process For Manufacturing the Same And Those Containing Antibiotically Active Composition. Sep. 30, 1974, DE 24 46 640). 135 mg or 270 mg of gentamicin pentakis dodecyl sulfate were dissolved in 1 g of methanol. The previously prepared methanol solution was dripped into the pores in each case of a square-shaped phosphate glass. The sample substances soaked up the solution and were subsequently dried at room temperature until mass constancy.

TABLE 1

Compositions of solutions used as well as weighing out of uncoated and coated sample substances from Examples 1 and 2

| Example No. | Composition of the solution | Mass of the sample elements before coating [mg] | Mass of the sample elements after coating [mg] | Mass of the coating [mg] |
|---|---|---|---|---|
| 1 | 135 mg GPDS 1000 mg methanol | 3949 | 4087 | 130 |
| 2 | 270 mg GPDS 1000 mg methanol | 3992 | 4257 | 265 |

GPDS: Gentamicin pentakis dodecyl sulfate

Antibiotics release of the sample elements from Examples 1 and 2:

The molded elements produced in examples 1 and 2 were added in each case to 20 ml of physiological saline and stored at 37° C. over a period of 28 days. Sampling took place after 1, 2, 3, 6, 9, 13, 15, 21 and 28 days of storage time. After each sampling, the releasing medium was completely replaced by fresh medium. Antibiotics determination was conducted with an agar diffusion test using *Bacillus subtilis* ATCC 6633 as a test germ. The results are presented in Tab. 2.

TABLE 2

Results of the microbial determination of gentamicin release of the coated sample elements of Examples 1 and 2 as a function of storage time of the sample elements in physiological saline at 37E C. Gentamicin release (cumulative, as gentamicin sulfate AK = 628) [mg]

Release time [d]

| Example No. | 1 | 2 | 3 | 6 | 9 | 13 | 15 | 21 | 28 |
|---|---|---|---|---|---|---|---|---|---|
| 1 | 1.2 | 1.9 | 2.7 | 3.8 | 4.9 | 5.8 | 6.9 | 8.1 | 9.2 |
| 2 | 1.5 | 3.1 | 4.3 | 5.4 | 6.7 | 7.9 | 8.8 | 10.1 | 11.4 |

What is claimed is:

1. Process for antibiotic coating of elements with interconnecting microcavities, comprising introducing into the microcavities a solution containing a solvent and 1) gentamicin dodecyl sulfate with 1 to 5 dodecyl sulfate groups per gentamicin molecule and/or 2) gentamicin dodecyl sulfonate with 1 to 5 dodecyl sulfonate groups per gentamicin molecule, and vaporizing or evaporating said solvent, obtaining on the surface of the microcavities a layer of gentamicin-dodecyl sulfate or gentamicin dodecyl sulfonate.

2. Process according to claim 1, wherein the solution comprises gentamicin pentakis dodecyl sulfate or gentamicin tetrakis dodecyl sulfate and/or gentamicin pentakis dodecyl sulfonate and/or gentamicin tetrakis dodecyl sulfonate.

3. Process according to claim 1, wherein the solvent is at least one organic solvent.

4. Process according to claim 3, wherein the solvent is at least one chemical selected from the group consisting of methanol, ethanol, N,N-dimethyl formamide and dimethyl sulfoxide.

5. Process according to claim 1, wherein said introducing takes place by dipping or spraying or dripping the solution.

6. Process according to claim 1, wherein the elements are synthesized of a substance selected from the group consisting of collagen, gelatin or polyester, calcium carbonate, calcium sulfate, tricalcium phosphate or hydroxyl apatite.

7. Process according to claim 1, wherein the solution additionally comprises one or more substances selected from the group consisting of ciprofloxacin dodecyl benzyl sulfonate and/or dodecyl sulfate and/or dodecyl sulfonates of clindamycin, tetracycline, lincosamine, chlortetracycline, oxytetracycline, demethyl chlortetracycline, methacycline, doxycycline, rolitetracycline and monocycline.

8. Process according to claim 1, which comprises introducing to the interconnecting microcavities first a diluted solution which compromises at least one antibiotic component lightly soluble in water from the group consisting of aminoglycoside antibiotics, the tetracycline antibiotics, the lincosamide antibiotics and the 4-quinolone antibiotics, and, subsequently, after evaporating and/or vaporizing the water, introducing into methanol, ethanol, N,N-dimethyl formamide and/or dimethyl sulfoxide by dipping or spraying or dripping a solution of gentamicin dodecyl sulfate or gentamicin dodecyl sulfonate.

9. Process according to claim 8, wherein the antibiotic component lightly soluble in water is selected from the group consisting of gentamicin sulfate, clindamycin hydrochloride, clindamycin dihydrogen phosphate, lincosamine hydrochloride, kanamycin sulfate, amikacin sulfate, tobramycin sulfate, tetracycline hydrochloride, chlortetracycline hydrochloride, oxytetracycline hydrochloride, dimethyl chlortetracycline hydrochloride, methacycline hydrochloride, doxycycline hydrochloride, rolitetracycline hydrochloride, minocycline hydrochloride and/or ciprofloxacin hydrochloride and/or moxifloxacin hydrochloride.

10. Process according to claim 8, wherein the solution is of gentamicin pentakis dodecyl sulfate and/or gentamicin tetrakis dodecyl sulfate and/or gentamicin pentakis dodecyl sulfonate and/or gentamicin tetrakis dodecyl sulfonate.

11. Process according to claim 1, wherein 0.1 to 20.0 percent by mass of dodecyl sulfate or sulfonate in relation to the solvent is introduced.

12. Process according to claim 1, wherein fleece, felts, hosiery or knit fabrics made of polyester, collagen or gelatins are antibiotically coated.

13. Process according to claim 1, wherein porous molded elements of polyesters, calcium carbonate, calcium sulfate, tricalcium phosphate, hydroxyl apatite or resorbable glass are coated.

14. Process according to claim 1, wherein metallic molded elements of titanium, titanium alloys or high-grade steel are coated.

* * * * *